US008983618B2

(12) United States Patent
Yamamoto et al.

(10) Patent No.: US 8,983,618 B2
(45) Date of Patent: Mar. 17, 2015

(54) CO-FIRED MULTI-LAYER ANTENNA FOR IMPLANTABLE MEDICAL DEVICES AND METHOD FOR FORMING THE SAME

(75) Inventors: Joyce K. Yamamoto, Maple Grove, MN (US); Gregory John Haubrich, Champlin, MN (US); Gerard J. Hill, Champlin, MN (US)

(73) Assignee: Medtronic, Inc., Minneapolis, MN (US)

( * ) Notice: Subject to any disclaimer, the term of this patent is extended or adjusted under 35 U.S.C. 154(b) by 1398 days.

(21) Appl. No.: 12/347,694

(22) Filed: Dec. 31, 2008

(65) Prior Publication Data
US 2010/0114246 A1    May 6, 2010

Related U.S. Application Data

(60) Provisional application No. 61/110,532, filed on Oct. 31, 2008.

(51) Int. Cl.
| A61N 1/08 | (2006.01) |
| H01Q 1/27 | (2006.01) |
| A61N 1/372 | (2006.01) |
| A61N 1/375 | (2006.01) |

(Continued)

(52) U.S. Cl.
CPC ............ *A61N 1/37223* (2013.01); *A61N 1/375* (2013.01); *H01Q 1/273* (2013.01); *H01Q 9/40* (2013.01); *H01Q 11/08* (2013.01)
USPC .................. 607/60; 607/30; 607/32

(58) Field of Classification Search
USPC .............................. 607/30, 32, 60
See application file for complete search history.

(56) References Cited

U.S. PATENT DOCUMENTS

| 5,023,624 A | 6/1991 | Heckaman et al. |
| 5,198,824 A | 3/1993 | Poradish |

(Continued)

FOREIGN PATENT DOCUMENTS

| EP | 1362614 A1 | 11/2003 |
| EP | 1508940 | 2/2005 |

(Continued)

OTHER PUBLICATIONS

Caiazzo, et al., A Metamaterial Surface for Compact Cavity Resonators, IEEE AP Letters, 2004, pp. 261-264, vol. 3.

(Continued)

*Primary Examiner* — Niketa Patel
*Assistant Examiner* — Christopher A Flory
(74) *Attorney, Agent, or Firm* — Michael J. Ostrom; Stephen W. Bauer

(57) ABSTRACT

An antenna for an implantable medical device (IMD) is provided including a monolithic structure derived from a plurality of discrete dielectric layers having an antenna embedded within the plurality of dielectric layers. The antenna includes antenna portions formed within different layers of the monolithic structure with at least one conductive via formed to extend through the dielectric layers in order to provide a conductive pathway between the portions of the antenna formed on different layers, such that an antenna is formed that extends between different vertical layers. The dielectric layers may comprise layers of ceramic material that can be co-fired together with the antenna to form a hermetically sealed monolithic antenna structure. The antenna embedded within the monolithic structure can be arranged to have a substantially spiral, helical, fractal, meandering or planer serpentine spiral shape.

22 Claims, 5 Drawing Sheets

(51) Int. Cl.
*H01Q 9/40* (2006.01)
*H01Q 11/08* (2006.01)

(56) References Cited

U.S. PATENT DOCUMENTS

| | | | |
|---|---|---|---|
| 5,219,377 | A | 6/1993 | Poradish |
| 5,387,888 | A | 2/1995 | Eda et al. |
| 5,620,476 | A | 4/1997 | Truex et al. |
| 5,861,019 | A | 1/1999 | Sun et al. |
| 6,107,227 | A | 8/2000 | Jacquin et al. |
| 6,320,547 | B1 | 11/2001 | Fathy et al. |
| 6,391,082 | B1 | 5/2002 | Holl |
| 6,398,710 | B1 | 6/2002 | Ishikawa et al. |
| 6,414,835 | B1 | 7/2002 | Wolf et al. |
| 6,415,184 | B1 | 7/2002 | Ishikawa et al. |
| 6,556,169 | B1 | 4/2003 | Fukuura et al. |
| 6,580,402 | B2 | 6/2003 | Navarro et al. |
| 6,759,920 | B1 | 7/2004 | Cheung et al. |
| 7,012,327 | B2* | 3/2006 | Huff et al. ............ 257/686 |
| 7,068,491 | B1* | 6/2006 | Burdon et al. ............ 361/313 |
| 7,122,891 | B2 | 10/2006 | Dishongh |
| 7,164,572 | B1 | 1/2007 | Burdon et al. |
| 7,289,063 | B2 | 10/2007 | Zaghloul |
| 7,317,946 | B2 | 1/2008 | Twetan et al. |
| 7,392,015 | B1 | 6/2008 | Farlow et al. |
| 8,050,771 | B2* | 11/2011 | Yamamoto et al. ........ 607/60 |
| 8,369,950 | B2* | 2/2013 | Rawat et al. ........... 607/32 |
| 8,497,804 | B2* | 7/2013 | Haubrich et al. ...... 343/700 MS |
| 2003/0011515 | A1 | 1/2003 | Warble et al. |
| 2004/0106967 | A1 | 6/2004 | Von Arx et al. |
| 2004/0215280 | A1 | 10/2004 | Dublin et al. |
| 2005/0109453 | A1 | 5/2005 | Jacobson et al. |
| 2006/0212096 | A1 | 9/2006 | Stevenson |
| 2006/0214855 | A1 | 9/2006 | Harada |
| 2007/0060969 | A1* | 3/2007 | Burdon et al. ............ 607/37 |
| 2007/0060970 | A1* | 3/2007 | Burdon et al. ............ 607/37 |
| 2007/0123949 | A1* | 5/2007 | Dabney et al. ........... 607/37 |
| 2007/0200706 | A1 | 8/2007 | Lee |
| 2007/0203529 | A1* | 8/2007 | Iyer et al. ............. 607/37 |
| 2007/0236861 | A1* | 10/2007 | Burdon et al. ............ 361/302 |
| 2007/0288066 | A1 | 12/2007 | Christman et al. |
| 2008/0021522 | A1 | 1/2008 | Verhoef et al. |
| 2008/0036668 | A1 | 2/2008 | White et al. |
| 2008/0195180 | A1 | 8/2008 | Stevenson et al. |
| 2009/0046028 | A1* | 2/2009 | Han et al. ............. 343/787 |
| 2009/0228074 | A1* | 9/2009 | Edgell et al. ........... 607/60 |
| 2009/0270948 | A1 | 10/2009 | Nghiem et al. |
| 2010/0109958 | A1* | 5/2010 | Haubrich et al. ......... 343/718 |
| 2010/0109966 | A1* | 5/2010 | Mateychuk et al. ....... 343/841 |
| 2010/0114245 | A1* | 5/2010 | Yamamoto et al. ........ 607/60 |
| 2010/0141360 | A1 | 6/2010 | Betts-Lacroix |
| 2013/0131752 | A1* | 5/2013 | Rawat et al. ........... 607/32 |

FOREIGN PATENT DOCUMENTS

| | | |
|---|---|---|
| WO | WO/01/02468 | 1/2001 |
| WO | 2005/076408 | 8/2005 |

OTHER PUBLICATIONS

Wu, et al., A study Using Metamaterials As Antenna Substrate to Enhance Gain, PIER 51, 2005, pp. 295-328.

Mosallaei, et al, Antenna Miniaturization and Bandwidth Enhancement Using a Reactive Impedance Substrate, IEEE APS, Sep. 2004, pp. 2403-2414, vol. 52 No. 9.

Broas, et al., A High Impedance Ground Plane Applied to a Cellphone Handset Geometry, IEEE MTT, Jul. 2001, pp. 1262-1265, vol. 49 No. 7.

Lal C. Godara, Application of Antenna Arrays to Mobile Communications, Part I: Performance Improvement, Feasibility, and System Considerations, Proceedings of the IEEE, Jul. 1997, pp. 1031-1060, vol. 85, No. 7.

Lal C. Godara, Application of Antenna Arrays to Mobile Communications, Part II: Beam-Forming and Direction-of-Arrival Considerations, Proceedings of the IEEE, Aug. 1997, pp. 1195-1245, vol. 85, No. 8.

P0032745.02 (PCT/US09/061760) PCT Notification of Transmittal of the International Search Report and the Written Opinion of the International Searching Authority, 12 pages.

* cited by examiner

CO-FIRED MULTI-LAYER ANTENNA FOR IMPLANTABLE MEDICAL DEVICES AND METHOD FOR FORMING THE SAME

RELATED APPLICATION

This application claims the benefit of and priority to U.S. Provisional Application Ser. No. 61/110,532, filed Oct. 31, 2008, entitled, "Co-fired Spiral Antenna For Implantable Medical Devices and Method for Forming the Same," the contents of which are incorporated by reference herein in its entirety.

TECHNICAL FIELD

The present invention relates generally to implantable medical devices (IMDs) and, more particularly, the present invention relates to telemetry antennas suitable for deployment in IMDs.

BACKGROUND

Various types of devices have been developed for implantation into the human body to provide various types of health-related therapies, diagnostics and/or monitoring. Examples of such devices, generally known as implantable medical devices (IMDs), include cardiac pacemakers, cardioverter/defibrillators, cardiomyostimulators, cardiac event monitors, various physiological stimulators including nerve, muscle, and deep brain stimulators, various types of physiological monitors and sensors, and drug delivery systems, just to name a few. IMDs typically include functional components contained within a hermetically sealed enclosure or housing, which is sometimes referred to as a "can." In some IMDs, a connector header or connector block is attached to the housing, and the connector block facilitates interconnection with one or more elongated electrical medical leads. The header block is typically molded from a relatively hard, dielectric, non-conductive polymer. The header block includes a mounting surface that conforms to, and is mechanically affixed against, a mating sidewall surface of the housing.

It has become common to provide a communication link between the hermetically sealed electronic circuitry of the IMD and an external programmer, monitor, or other external medical device ("EMD") in order to provide for downlink telemetry transmission of commands from the EMD to the IMD and to allow for uplink telemetry transmission of stored information and/or sensed physiological parameters from the IMD to the EMD. Conventionally, the communication link between the IMD and the EMD is realized by encoded radio frequency ("RF") transmissions between an IMD telemetry antenna and transceiver and an EMD telemetry antenna and transceiver. Generally, for inductive telemetry, the IMD antenna is disposed within the hermetically sealed housing; however, the typically conductive housing adversely attenuates the radiated RF field and limits the data transfer distance between the programmer head and the IMD RF telemetry antennas to a few inches. This type of system may be referred to as a "near field" telemetry system. In order to provide for "far field" telemetry, or telemetry over distances of a few to many meters from an IMD or even greater distances, attempts have been made to provide antennas outside of the hermetically sealed housing and within the header block. Many of such attempts of positioning an RF telemetry antenna outside of the hermetically sealed housing and in the header block have utilized wire antennas or planar, serpentine antennas, such as the antennas described in U.S. Pat. No. 7,317,946, which is hereby incorporated by reference in its entirety.

SUMMARY

In one or more embodiments, an antenna for an implantable medical device (IMD) is provided including a monolithic structure derived from a plurality of discrete dielectric layers having an antenna embedded within multiple layers of the plurality of dielectric layers. The antenna includes antenna portions positioned in different layers of the monolithic antenna structure. At least one conductive via is formed to extend through the dielectric layers in order to provide a conductive pathway between the portions of the antenna on different layers of the monolithic antenna structure. In this manner, an antenna is formed that extends between different vertical layers of the structure. In one or more embodiments, the portions of the antenna positioned on different layers of the monolithic structure and the vias interconnecting these antenna portions are arranged to form an antenna having a substantially spiral or helical shape embedded within the monolithic structure. In some embodiments, the portions of the antenna positioned on different layers of the monolithic structure and the vias interconnecting these antenna portions are arranged to form an antenna having fractal, meandering, planer serpentine spiral or other three-dimensional (3D) multi-layer antenna shapes. The specific configuration, number of layers, number of vias, RF characteristics, antenna gain, and other operational features of the antenna structure are selected to suit the needs of the particular IMD and/or the particular implant location.

In one or more embodiments, the dielectric layers comprise at least one of a low temperature co-fire ceramic (LTCC) material and/or a high temperature co-fire ceramic (HTCC) material (and/or Liquid Crystal Polymer, LCP, glass, or other insulating dielectric layers) where the ceramic dielectric layers, the portions of the antenna formed on various layers of the structure and the interconnecting vias are co-fired or bonded together to form a monolithic antenna structure. In some embodiments, the size, configuration and material selected for the interconnecting vias can be variably selected to achieve a desired impedance of the antenna. In some embodiments, at least one location (or cavity) is formed in the monolithic structure with respect to the embedded antenna to provide space for embedded radio frequency (RF) impedance matching elements. This location may be in the form of a cavity or may contain embedded passives or distributed transmission line impedance matching structures embedded in the monolithic structure material or may further contain other control modules within the cavity location.

DRAWINGS

The above-mentioned features and objects of the present disclosure will become more apparent with reference to the following description taken in conjunction with the accompanying drawings wherein like reference numerals denote like elements and in which.

DETAILED DESCRIPTION

The following detailed description is merely illustrative and is not intended to limit the invention or the application and uses of the invention. Furthermore, there is no intention to be bound by any expressed or implied theory presented in the preceding technical field, background, brief summary or the following detailed description.

The following description refers to components or features being "connected" or "coupled" together. As used herein, unless expressly stated otherwise, "connected" means that one component/feature is directly or indirectly connected to another component/feature, and not necessarily mechanically. Likewise, unless expressly stated otherwise, "coupled" means that one component/feature is directly or indirectly coupled to another component/feature, and not necessarily mechanically. Thus, although the figures may depict example arrangements of elements, additional intervening elements, devices, features, or components may be present in an actual embodiment (assuming that the functionality of the IMDs are not adversely affected).

In one or more embodiments, an IMD having a three dimensional (3D) antenna embedded within a monolithic structure is provided. For the sake of brevity, conventional techniques and aspects related to RF antenna design, IMD telemetry, RF data transmission, signaling, IMD operation, connectors for IMD leads, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in a practical embodiment.

An IMD antenna generally has two functions: to convert the electromagnetic power of a downlink telemetry transmission of an EMD telemetry antenna propagated through the atmosphere (and then through body tissues) into a signal (e.g., a UHF signal or the like) that can be processed by the IMD transceiver into commands and data that are intelligible to the IMD electronic operating system; and to convert the uplink telemetry signals (e.g., a UHF signal or the like) of the IMD transceiver electronics into electromagnetic power propagated through the body tissue and the atmosphere so that the EMD telemetry antenna or antennas can receive the signals.

Figure 1:
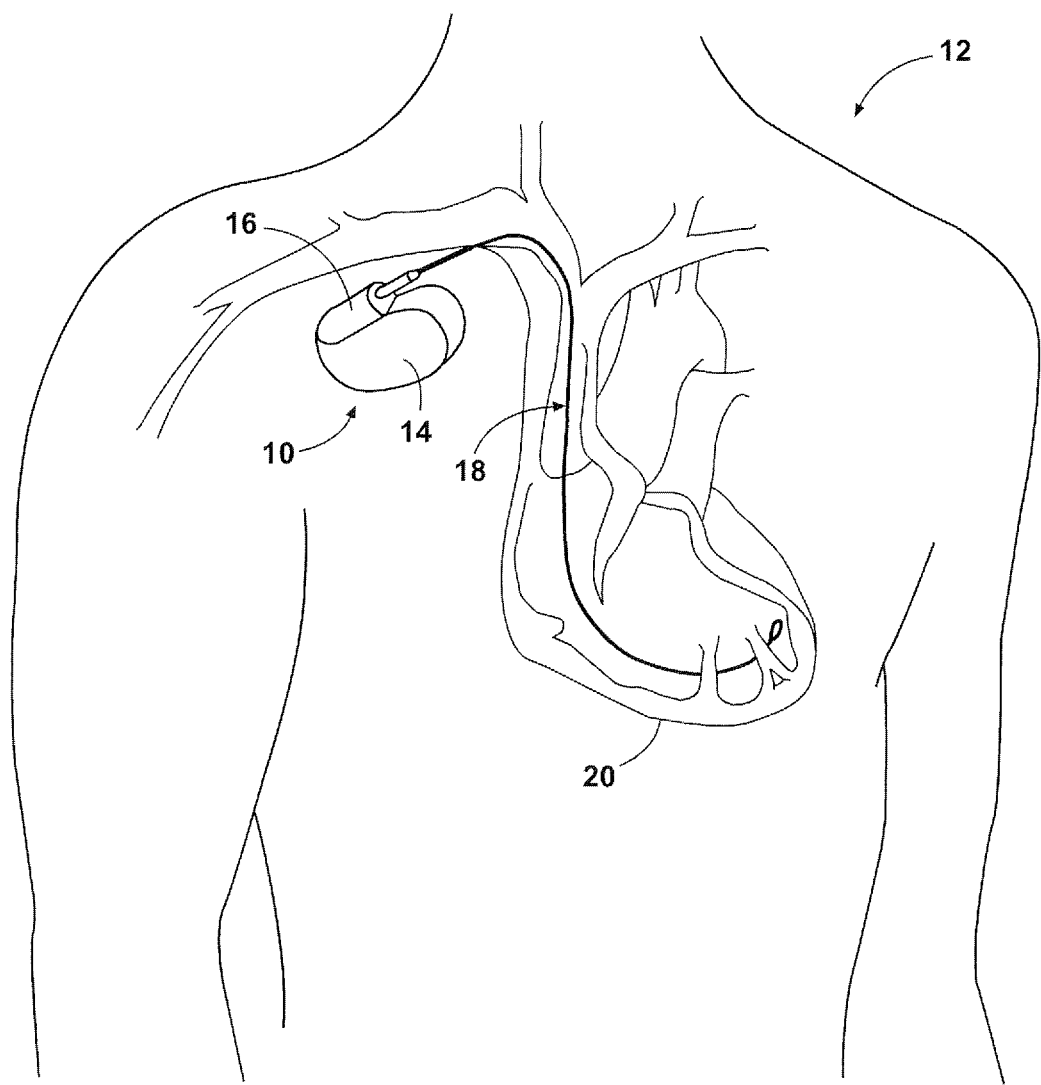
FIG. 1 illustrates an implantable medical device implanted in a human body in accordance with one or more embodiments of the present disclosure.

FIG. 1 is a perspective view of an IMD 10 implanted within a human body 12 in which one or more embodiments of the invention may be implemented. IMD 10 comprises a hermetically sealed housing 14 (or "can") and connector header or block module 16 for coupling IMD 10 to electrical leads and other physiological sensors arranged within body 12, such as pacing and sensing leads 18 connected to portions of a heart 20 for delivery of pacing pulses to a patient's heart 20 and sensing of heart 20 conditions in a manner well known in the art. For example, such leads may enter at an end of header block 16 and be physically and electrically connected to conductive receptacles, terminals, or other conductive features located within header block 16. IMD 10 may be adapted to be implanted subcutaneously in the body of a patient such that it becomes encased within body tissue and fluids, which may include epidermal layers, subcutaneous fat layers, and/or muscle layers. While IMD 10 is depicted in FIG. 1 in an ICD configuration, it is understood that this is for purposes of illustration only and IMD 10 may comprise any type of medical device requiring a telemetry antenna.

In some embodiments, hermetically sealed housing 14 is generally circular, elliptical, prismatic, or rectilinear, with substantially planar major sides joined by perimeter sidewalls. Housing 14 is typically formed from pieces of a thin-walled biocompatible metal such as titanium. Two half sections of housing 12 may be laser seam welded together using conventional techniques to form a seam extending around the perimeter sidewalls. Housing 14 and header block 16 are often manufactured as two separate assemblies that are subsequently physically and electrically coupled together. Housing 14 may contain a number of functional elements, components, and features, including (without limitation): a battery; a high voltage output capacitor; integrated circuit ("IC") devices; a processor; memory elements; a therapy module or circuitry; an RF module or circuitry; and an antenna matching circuit. These components may be assembled in spacers and disposed within the interior cavity of housing 14 prior to seam welding of the housing halves. During the manufacturing process, electrical connections are established between components located within housing 14 and elements located within header block 16. For example, housing 14 and header block 16 may be suitably configured with IC connector pads, terminals, feedthrough elements, and other features for establishing electrical connections between the internal therapy module and the therapy lead connectors within header block 16 and for establishing connections between the internal RF module and a portion of a telemetry antenna located within header block 16. Structures and techniques for establishing such electrical (and physical) feedthrough connections are known to those skilled in the art and, therefore, will not be described in detail herein. For example, U.S. Pat. No. 6,414,835 describes a capacitive filtered feedthrough array for an implantable medical device, the contents of which are hereby incorporated by reference.

Header block 16 is preferably formed from a suitable dielectric material, such as a biocompatible synthetic polymer. In some embodiments, the dielectric material of header block 16 may be selected to enable the passage of RF energy that is either radiated or received by a telemetry antenna (not shown in FIG. 1) encapsulated within header block 16. The specific material for header block 16 may be chosen in response to the intended application of IMD 10, the electrical characteristics of the environment surrounding the implant location, the desired operating frequency range, the desired RF antenna range, and other practical considerations.

Figure 2:
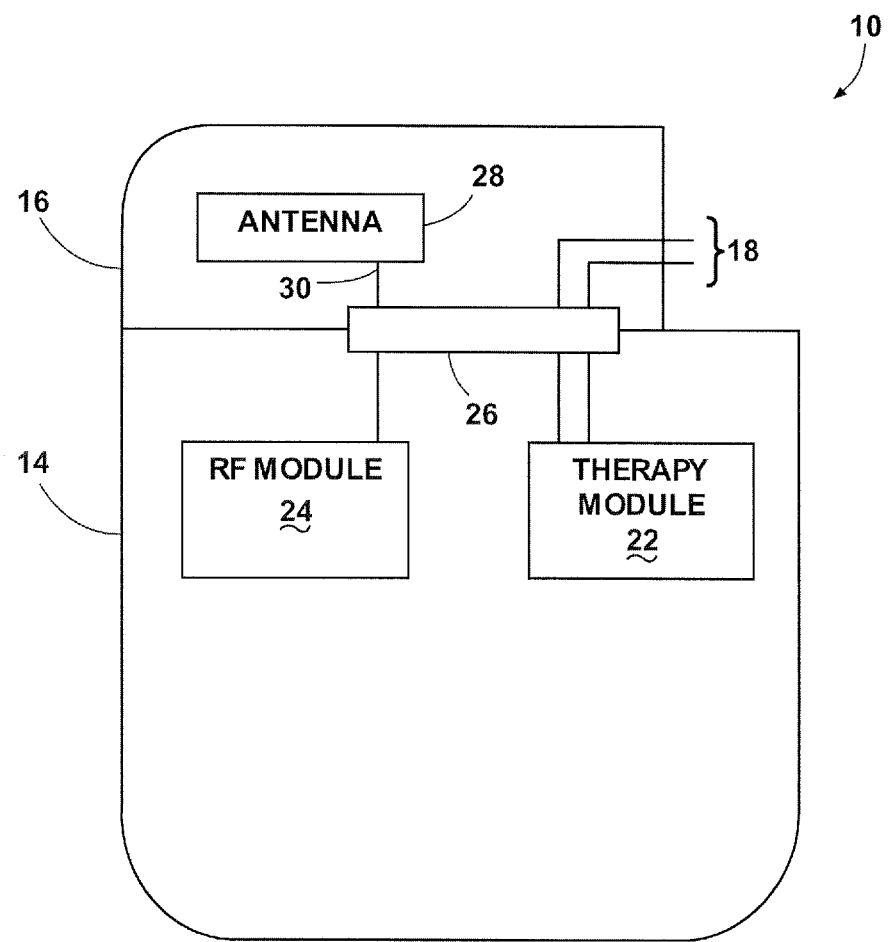
FIG. 2 is a schematic block diagram illustration of exemplary implantable medical device in accordance with one or more embodiments of the present disclosure.

FIG. 2 is a simplified schematic representation of an IMD 10 and several functional elements associated therewith. IMD 10 generally includes hermetically sealed housing 14 and header block 16 coupled to housing 14, a therapy module 22 contained within housing 14, and an RF module 24 contained within housing 14. In practice, IMD 10 will also include a number of conventional components and features necessary to support the functionality of IMD 10 as known in the art. Such conventional elements will not be described herein.

Therapy module 22 may include any number of components, including, without limitation: electrical devices, ICs, microprocessors, controllers, memories, power supplies, and the like. Briefly, therapy module 22 is configured to provide the desired functionality associated with the IMD 10, e.g., defibrillation pulses, pacing stimulation, patient monitoring, or the like. In this regard, therapy module 22 may be coupled to one or more sensing or therapy leads 18. In practice, the connection ends of therapy leads 18 are inserted into header block 16, where they establish electrical contact with conductive elements coupled to therapy module 22. Therapy leads 18 may be inserted into suitably configured lead bores formed within header block 16. In the example embodiment, IMD 10 includes a feedthrough element 26 that bridges the transition between housing 14 and header block 16. Therapy leads 18 extend from header block 16 for routing and placement within the patient.

RF module 24 may include any number of components, including, without limitation: electrical devices, ICs, amplifiers, signal generators, a receiver and a transmitter (or a transceiver), modulators, microprocessors, controllers, memories, power supplies, and the like. RF module 24 may further include a matching circuit. Briefly, RF module 24 supports RF telemetry communication for IMD 10, including, without limitation: generating RF transmit energy; providing RF transmit signals to antenna 28; processing RF telemetry signals received by antenna 28, and the like. In practice, RF module 28 may be designed to leverage the conductive material used for housing 14 as an RF ground plane (for some applications), and RF module 24 may be designed in accordance with the intended application of IMD 10, the electrical characteristics of the environment(s) surrounding IMD 10, the desired operating frequency range, the desired RF antenna range, and other practical considerations.

Antenna 28 is coupled to RF module 24 to facilitate RF telemetry between IMD 10 and an EMD (not shown). Generally, antenna 28 is suitably configured for RF operation (e.g., UHF or VHF operation, 401 to 406 MHz for the MICS/MEDS bands, and/or 900 MHz/2.4 GHz and/or other ISM bands, etc.). In the example embodiment shown in FIG. 2, antenna 28 is located within header block 16 and outside of housing 14. In one or more embodiments, antenna 28 is coupled to RF module 24 via an RF feedthrough in feedthrough 26, which bridges housing 14 and header block 16. Antenna 28 may include a connection end 30 that is coupled to RF feedthrough in feedthrough 26 via a conductive terminal or feature located within header block 16. Briefly, a practical feedthrough 26 includes a ferrule supporting a nonconductive glass or ceramic annular insulator. The insulator supports and electrically isolates a feedthrough pin from the ferrule. During assembly of housing 14, the ferrule is welded to a suitably sized hole or opening formed in housing 14. RF module 24 is then electrically connected to the inner end of the feedthrough pin. The connection to the inner end of the feedthrough pin can be made by welding the inner end to a substrate pad, or by clipping the inner end to a cable or flex wire connector that extends to a substrate pad or connector. The outer end of the feedthrough pin serves as a connection point for antenna 28, or as a connection point for an internal connection socket, terminal, or feature that receives the connection end 30 of antenna 28. Header block 16 and feedthrough 26 may be located on any desired portion of housing 14 suitable for a particular design.

Figure 3:
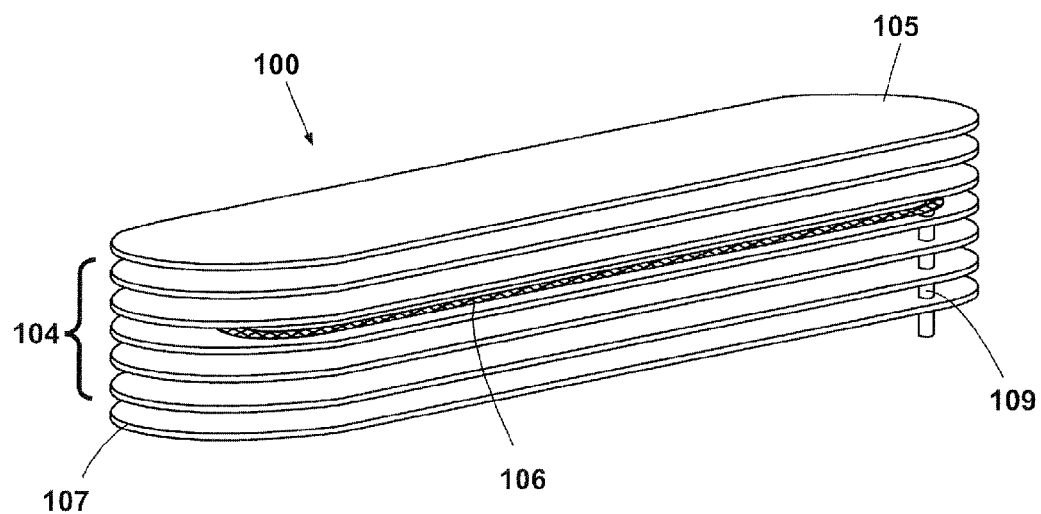
FIG. 3 is a perspective, exploded view of an antenna structure for an implantable medical device formed in accordance with one or more embodiments of the present disclosure.

Referring now to FIG. 3, a perspective, exploded view of an antenna structure 100 formed in accordance with one or more embodiments is respectively illustrated. Certain features and aspects of antenna structure 100 are similar to those described above in connection with antenna 28, and shared features and aspects will not be redundantly described in the context of antenna structure 100. Antenna structure 100 is derived from a plurality of discrete dielectric layers 104, wherein an antenna 106 is positioned, arranged and/or formed on one or more the plurality of dielectric layers 104. In one or more embodiments, the dielectric layers 104 on which the antenna 106 is formed and also those dielectric layers 104 arranged both above and below the antenna can be selected to possess dielectric constants that provide an improved matching gradient between the antenna 106 and the surrounding environment (e.g., the surrounding body tissue in the case of an IMD 10) and/or the hermetically sealed housing 14. For instance, the dielectric layers 104 formed above the antenna 106 may include dielectric constants that optimize antenna performance for the surrounding environment, while the dielectric layers 104 formed below the antenna 106 may include dielectric constants which also optimize antenna performance. This optimization may include gradual changes in each dielectric layer 104 to facilitate matching to the media above the antenna 106 and the hermetic sealed housing 14 below. This improved matching gradient between the antenna 106 and the surrounding environment mitigates the energy reflection effect that otherwise occurs in conventional antenna structures possessing abrupt transitions and differences in dielectric constants at the boundary between the antenna structures and the surrounding environment.

In one or more embodiments, antenna structure 100 may include an outermost layer 105 formed of a biocompatible material that is selected to serve as an interface with the surrounding environment, where different types of biocompatible materials can be selected based on the intended use of antenna structure 100 and IMD 10 and the intended surrounding environment. For example, outermost layer 105 may comprise inorganic materials, such as Alumina ($Al_2O_3$), zirconium oxide ($ZrO_2$), mixtures thereof, or bone-like systems [hydroxyapatite-$Ca_5(POH)(PO_4)_3$], organic materials, such as silicone and its derivatives, and other traditionally implantable biocompatible materials. In one or more embodiments, antenna structure 100 may include an innermost shield layer 107 formed from a metalized material that provides electromagnetic shielding of device circuitry inside of the hermetically sealed housing 14 to which the antenna structure 100 is attached through a feedthrough via 109. In one or more embodiments, the edges of the dielectric layers 104, outermost biocompatible layer 105 and innermost shielding layer 107 may be brazed or otherwise sealed to hermetically seal the edges of the antenna structure 100. Generally, brazing involves melting and flowing a brazing material (e.g., a metal such as gold) around the portions of the desired surfaces to be brazed (e.g., the edges of antenna structure 100).

Figure 4:
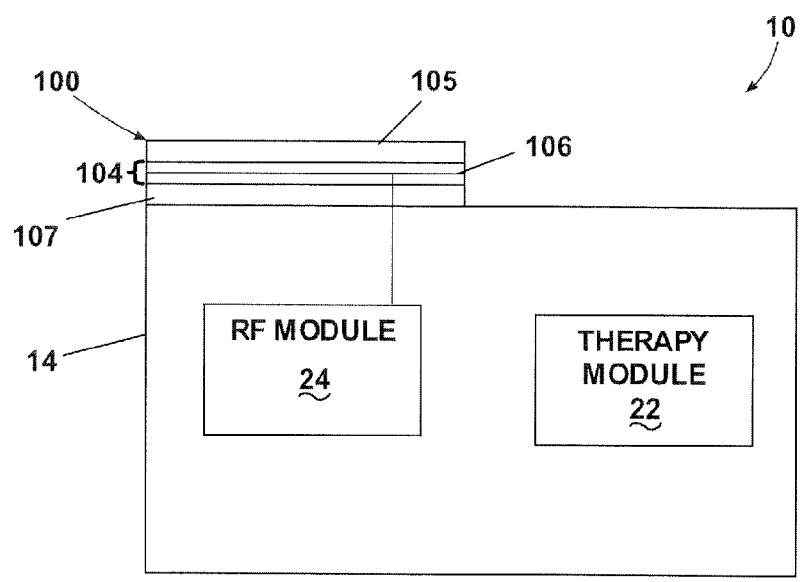
FIG. 4 is a schematic block diagram illustration of the antenna structure of FIG. 3 connected to implantable medical device in accordance with one or more embodiments of the present disclosure.

In one or more embodiments, antenna structure 100 may be directly connected to hermetically sealed housing 14 as illustrated in FIG. 4. The biocompatible outermost layer 105 and the brazed edges of antenna structure 100 provide a hermetic seal for antenna structure 100 so that it can be connected directly to housing 14 without requiring a header to enclose and seal the antenna, as typically required with conventional far field telemetry antennas for IMDs. Antenna structure 100 may be coupled to housing 14 using brazing, glassing, diffusion bonding or other suitable bonding techniques that will provide a hermetic seal, as known to those skilled in the art. The antenna structure 100 thus reduces the overall volume and physical dimension required for the antenna conductor for adequate radiation. In some embodiments, antenna structure 100 may still be positioned within a header block 16 if so desired. In some embodiments, antenna structure 100 may be bonded directly to housing 14 with at least a portion of antenna structure 100 in contact with a header block 16.

Figure 5:
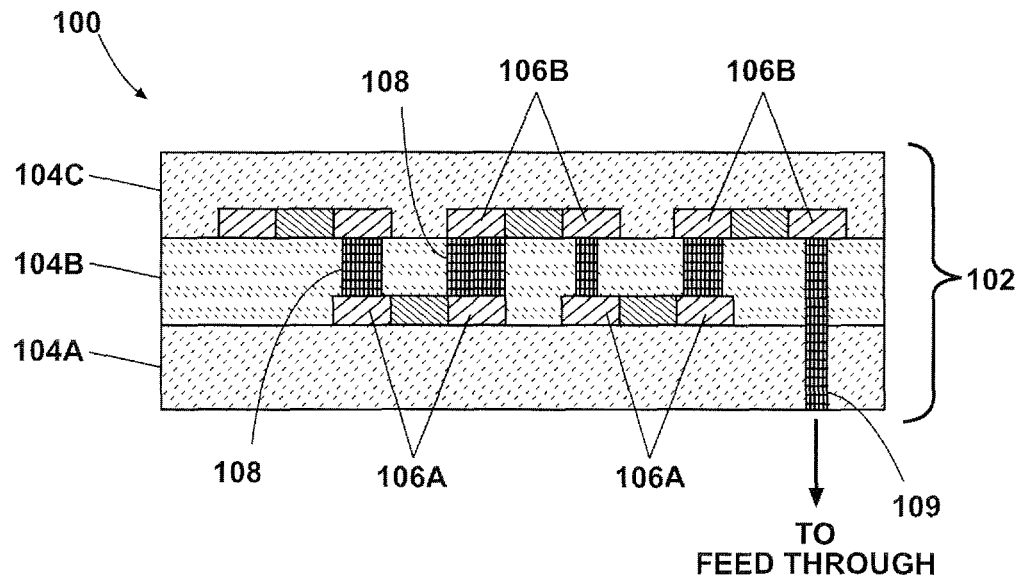
FIG. 5 is a cross-sectional view of an antenna structure for an implantable medical device formed in accordance with one or more embodiments of the present disclosure.
Figure 6:
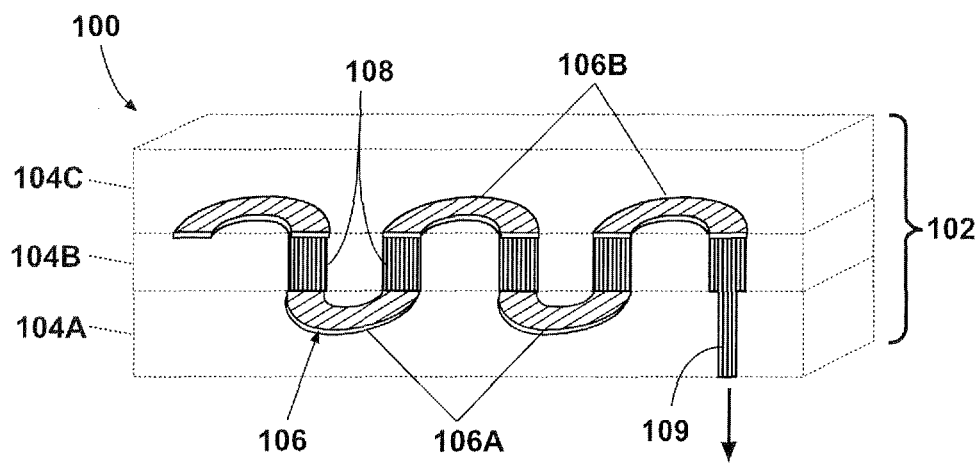
FIG. 6 is a perspective partial cutaway view of an antenna structure for an implantable medical device formed in accordance with one or more embodiments of the present disclosure.

Referring now to FIGS. 5 and 6, a cross-sectional side view and a perspective partial cut-away view of an antenna structure 100 formed in accordance with one or more embodiments are respectively illustrated. Certain features and aspects of antenna structure 100 are similar to those described above in connection with antenna 28, and shared features and aspects will not be redundantly described in the context of antenna structure 100. In one or more embodiments, antenna structure 100 for IMD 10 is provided including a monolithic structure 102 derived from a plurality of discrete dielectric layers 104 (e.g., 104a, 104b, 104c, etc.) having at least a portion of antenna 106 embedded within one or more layers of the plurality of discrete dielectric layers 104. In one or more embodiments, antenna 106 is made of a conductive material that can be suitably co-processed with the material for dielectric layers 104. The antenna 106 includes at least a first portion 106a located on one layer of the monolithic structure 102, such as positioned under a selected one 104b of the plurality of dielectric layers 104, and a second portion 106b located on another layer of the monolithic structure 102, such as positioned over the selected one 104b of the plurality of dielectric layers. While many embodiments described herein will be described with reference to two antenna portions 106a and 106b formed on two different layers of the antenna structure 100, it is understood that the antenna 106 may include any greater number of antenna portions formed on additional layers of the antenna structure 100.

At least one conductive via 108 is formed in at least one corresponding hole or aperture formed to extend through the selected one 104b of the plurality of dielectric layers 104 in order to provide an interconnecting conductive pathway between the first portion 106a and the second portion 106b of the antenna 106. It is understood that each of the first portion 106a and the second portion 106b may comprise a single tracing of conductive material or multiple separate tracings of conductive material that are patterned in a desired shape and interconnected to form a single continuous antenna 106. The first and second antenna portions 106a and 106b together with the interconnecting conductive vias 108 form a 3D antenna 106 that extends vertically through multiple layers of the monolithic antenna structure 100. In one or more embodiments, the antenna 106 is formed to come into contact with multiple dielectric layers 104 of antenna structure 100. A connection end 109, such as a conductive via or pin, further connects the antenna 106 to the feedthrough 26.

In one or more embodiments, the specific configuration of the first and second antenna portions 106a and 106b, the number of antenna portions (e.g., more than two antenna portions on more than two layers), the number of dielectric layers 104, the number of vias 108, the shape and configuration of vias 108, RF characteristics, antenna gain, and other operational features of the overall antenna structure 100 are selected to suit the needs of the particular IMD 10 and/or the particular implant location. In one or more embodiments, the first and second antenna portions 106a and 106b are formed from a biocompatible conductive material that is configured together with the interconnecting vias 108 to form an antenna 106 having an overall substantially spiral or helical shape. A spiral or helical antenna 106 that extends three dimensionally within the antenna structure 100 is advantageous in that it can possess a wide bandwidth, is capable of high gain and circular polarization, and allows a greater length of the antenna 106 to be achieved within a given volume than conventional planar antenna configurations. Other embodiments would include 2-D or 3-D fractal, planer serpentine meandering line, or other space saving patterns for the antenna conductor 106.

In one or more embodiments, in order to control the impedance of the antenna 106, the size, shape and materials used to form vias 108 can be variably selected, both individually and collectively, so that each individual via 108 can have its impedance variably selected to impact the overall impedance of the antenna 106. As can be seen in FIG. 5, vias 108 of different sizes or widths are illustrated to demonstrate the fact that the size of vias 108 can be variably selected. It is understood that vias 108 can have their size, shape and forming materials to be selected collectively or separately based on the desired characteristics of vias 108. Furthermore, each via 108 could be formed as a plurality of separate vias (i.e., sub-vias) connecting a portion of first antenna portion 106a to second antenna portion 106b to achieve a variable cross-sectional area. The collective cross-sectional area of the separate sub-vias represents the total cross-sectional area for the corresponding via 108. In this manner, the overall impedance of the antenna 106 can be more precisely selected to suit the needs of the antenna structure 100 for the particular IMD 10 and/or the particular implant location.

In one or more embodiments, the biocompatible conductive material used to form the first and second antenna portions 106a and 106b and vias 108 may include at least one of the following materials: Platinum, Iridium, Platinum-Iridium alloys, Alumina, Silver, Gold, Palladium, Silver-Palladium or mixtures thereof, Molybdenum and/or Moly-manganese or other suitable materials. In one or more embodiments, vias 108 may be formed by depositing the same biocompatible conductive material as the material used to form the first and second antenna portions 106a and 106b or may comprise a different biocompatible conductive material.

Figure 7:
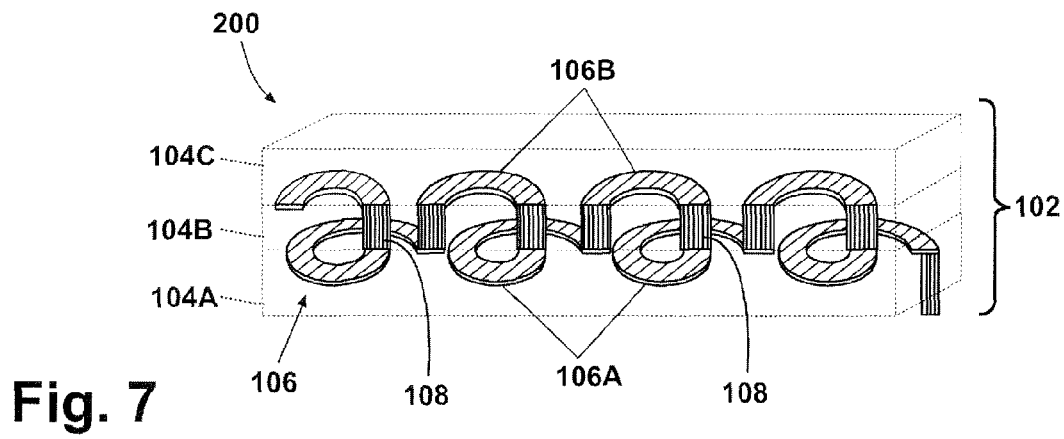
FIG. 7 is a perspective partial cutaway view of another antenna structure for an implantable medical device formed in accordance with one or more embodiments of the present disclosure.

In one or more embodiments, configurations, arrangements and/or patterns of the first and second antenna portions 106a and 106b may further be selected to achieve a desired impedance (i.e., inter-digiated capacitance) between the first and second antenna portions 106a and 106b in the antenna structure 100. For example, FIG. 7 illustrates an antenna structure 200 (similar in almost all features and aspects as antenna structure 100) having a spiral antenna 106 having first and second antenna portions 106a and 106b with substantially more overlapping regions than the antenna structure 100 illustrated in FIG. 5.

Figure 8:
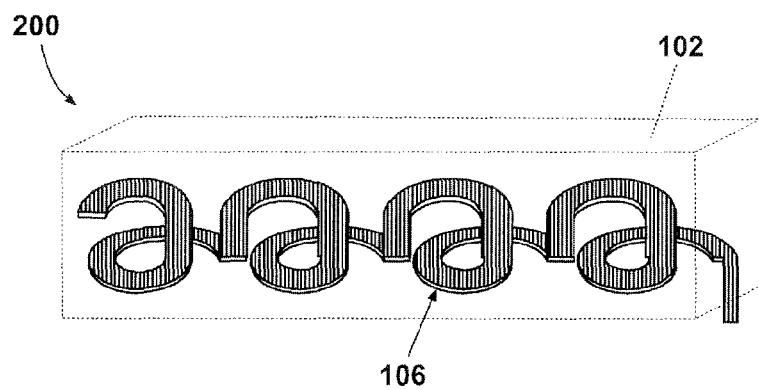
FIG. 8 is a perspective partial cutaway view of a resulting monolithic structure for an antenna for an implantable medical device formed in accordance with one or more embodiments of the present disclosure.

In one or more embodiments, the monolithic structure 102 is derived and formed from a plurality of dielectric layers 104. In one or more embodiments, the dielectric layers 104 may include at least one of a ceramic material, a semiconductor material, and/or a thick film dielectric material. In some embodiments in which the dielectric layers 104 include at least one ceramic material, the dielectric layers 104 may include at least one of a low temperature co-fire ceramic (LTCC) material or a high temperature co-fire ceramic (HTCC) material. Generally, a LTCC material has a melting point between about 850 C.° and 1150 C.°, while a HTCC material has a melting point between about 1100 C.° and 1700 C.°. In one or more embodiments, when a LTCC material is used for the dielectric layers 104, a biocompatible outermost layer 105 is positioned to be in contact with the body to provide the desired level of biocompatibility for the antenna structure 100. The ceramic dielectric layers 104, the first and second portions 106a and 106b of the antenna 106, and the interconnecting vias 108 are sintered or co-fired together to form a monolithic antenna structure 102 including an embedded antenna 106, as illustrated in FIG. 8. Methods for co-firing layers of ceramic materials together to form monolithic structures for use in IMDs are described, for example, in U.S. Pat. Nos. 6,414,835 and 7,164,572, the contents of both of which are hereby incorporated by reference in their entireties.

According to one or more embodiments, the use of a co-firing technique to form a monolithic antenna structure 102 including an embedded antenna 106 allows for the manufacture of low-cost, miniaturized, hermetically sealed antenna structures suitable for implantation within tissue and/or in direct or indirect contact with diverse body fluids. The monolithic antenna structure 102 can be hermetically sealed within header block 16 or alternatively directly to a portion of housing 14 of an IMD 10, and the monolithic antenna structure 102 can connect to internal circuitry, external circuitry and/or other components and can further be directly and/or indirectly exposed to living tissue and body fluids. In some embodiments, the monolithic antenna structure 100 can be connected to housing 14 without requiring a surrounding header block 16.

In one or more embodiments, the monolithic antenna structure 102 is derived and formed from a plurality of different individual discrete sheets of materials (or segments of tape) that comprise ceramic layers for the dielectric layers 104 and metal conductor layers for forming the antenna 106. The sheets of materials (or segments of tape) may be printed with a metalized paste and other circuit patterns, stacked on each other, laminated together and subjected to a predetermined temperature and pressure regimen, and then fired at an elevated temperature(s) during which the majority of binder material(s) (present in the ceramic) and solvent(s) (present in the metalized paste) vaporizes and/or is incinerated while the remaining material fuses or sinters. In some embodiments, the materials suitable for use as cofireable conductors for forming the antenna 106 are the biocompatible metal materials described herein or other materials suitable for the metalized paste.

In one or more embodiments, the dielectric layers 104 include a plurality of planar ceramic layers. Each ceramic layer may be shaped in an unfired or green state to have a layer thickness and a plurality of holes extending there through between an internally facing layer surface and an externally facing layer surface for accommodating vias 108. In general, the formation of planar ceramic layers starts with a ceramic slurry formed by mixing a ceramic particulate, a thermoplastic or thermoset polymer and solvents. This slurry is spread into ceramic sheets of predetermined thickness, from which the solvents are volatilized, leaving self-supporting flexible green sheets. Holes that will be filled with conductive material to form the vias 108 are made, using any conventional technique, such as drilling, punching, laser cutting, etc., through the green sheets from which the ceramic layers 104 are formed. The materials suitable for use as cofireable ceramics include alumina ($Al_2O_3$), aluminum nitride, beryllium oxide, Silica ($SiO_2$), Zirconia ($ZrO_2$), glass-ceramic materials, glass suspended in an organic (polymer) binder, or mixtures thereof.

Referring back to FIG. 5, when forming the layers used to form the monolithic antenna structure 102, at least one ceramic green sheet used for a dielectric layer 104A is formed, and a cofireable biocompatible metal conductor material used for the first antenna portion 106A formed there over by depositing, spraying, screening, dipping, plating, etc. the biocompatible metal conductor in a desired pattern on the dielectric layer 104A. Another ceramic green sheet used for a dielectric layer 104B is formed and patterned (including forming holes for vias 108) and then stacked and aligned in an appropriate laminated configuration over the first antenna portion 106A and dielectric layer 104A. The vias 108 are then formed by filling the patterned holes in the dielectric layer 104B with the cofireable biocompatible metal conductor material. The second antenna portion 106B is then formed from the cofireable biocompatible metal conductor material on dielectric layer 104B, where second antenna portion 106B is patterned, aligned and stacked in an appropriate laminated configuration over the first antenna portion 106A, vias 108 and dielectric layer 104B. A third ceramic green sheet used for a dielectric layer 104C is formed, stacked and aligned in an appropriate laminated configuration over the second antenna portion 106B and dielectric layer 104B. This process can be repeated for any number of additional dielectric layers 104 and/or layers of cofireable biocompatible metal conductor material used to form the 3D antenna 106 based upon a desired number of layers. In one or more embodiments, the stacked laminates are then co-fired together at temperatures between about 850 C.° and 1150 C.° for LTCC and between about 1100 C.° and 1700 C.° for HTCC.

Figure 9:
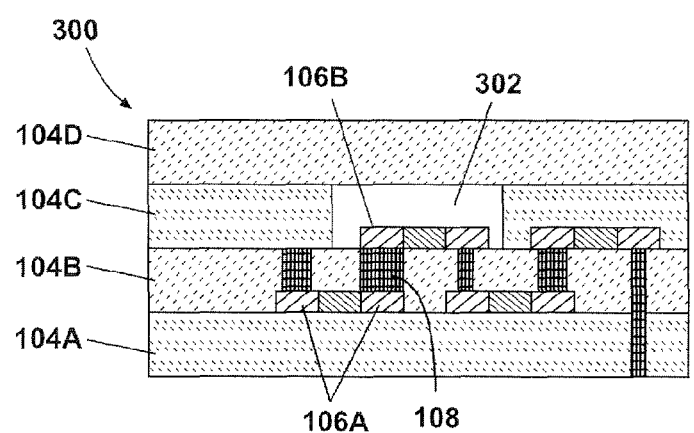
FIG. 9 is a cross-sectional view of another antenna structure for an implantable medical device formed in accordance with one or more embodiments of the present disclosure.

Referring now to FIG. 9, a partial cross-sectional side view of an antenna structure 300 formed in accordance with one or more embodiments is illustrated having at least one location (or cavity) 302 formed in the monolithic structure 102 for purposes of impedance matching. By forming a location (or cavity) 302 in one or more regions of the monolithic structure 102 with respect to the embedded antenna 106, radio frequency (RF) impedance matching functionality for the antenna 106 can be provided according desired characteristics. Further, this allows impedance matching functionality to be embedded within the monolithic structure 102 itself, so that impedance matching circuitry can be eliminated from within the housing 14. The impedance matching circuitry may be a cavity and/or may include both lumped element or distributed element impedance matching circuitry. In some embodiments, surface mounted elements or circuitry mounted on a surface of monolithic structure 102 can be utilized to provide alternative impedance matching functionality instead of relying on embedded elements within the monolithic structure 102 or such surface mounted elements or circuitry can be used in conjunction with the embedded elements to provide additional impedance matching functionality.

The use of a multi-layer-ceramic antenna structure 100 comprised of co-fired materials provide for reduced antenna volume, increased device density and functionality, and the ability to provide embedded antenna functionality, all in a hermetically-sealed monolithic antenna structure 102.

While the system and method have been described in terms of what are presently considered to be specific embodiments, the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

The invention claimed is:
1. An implantable medical device ("IMD"), comprising:
 a housing defining an interior cavity;

a monolithic antenna structure located outside of the housing, wherein the monolithic antenna structure is derived from:
  a plurality of discrete dielectric layers, and
  a three dimensional ("3D") antenna, wherein the 3D antenna comprises an antenna pattern that is embedded within the monolithic antenna structure and is in contact with multiple layers of the plurality of discrete dielectric layers, wherein a first portion of the 3D antenna pattern is positioned under a selected one of the plurality of dielectric layers, a second portion of the 3D antenna pattern is positioned over the selected one of the plurality of dielectric layers, and wherein at least one conductive via extending through the selected one of the plurality of dielectric layers that connects the first portion of the 3D antenna pattern to the second portion of the 3D antenna pattern; and
  a radio frequency (RF) module disposed within the interior cavity of the housing and electrically connected to the monolithic antenna structure, wherein the 3D antenna is configured to convert electromagnetic power of a downlink telemetry transmission of an external telemetry antenna into a signal that the RF module can process and to convert uplink telemetry signals generated by the RF module into electromagnetic power of an uplink telemetry transmission.

2. The IMD of claim 1, wherein the first and second portions of the 3D antenna pattern and the at least one conductive via are arranged such that the 3D antenna pattern possesses a substantially spiral or helical shape within the monolithic structure derived from the plurality of discrete dielectric layers.

3. The IMD of claim 1, wherein the first and second portions of the 3D antenna pattern and the at least one conductive via are arranged such that the 3D antenna pattern possesses at least one of a fractal, meandering or planer serpentine spiral shape within the monolithic structure derived from the plurality of discrete dielectric layers.

4. The IMD of claim 1, wherein at least one of the dielectric layers comprises a ceramic material.

5. The IMD of claim 4, wherein the dielectric layers, the first and second portions of the 3D antenna pattern, and the at least one conductive via are co-fired together.

6. The IMD of claim 1, wherein at least one of the dielectric layers comprises a low temperature co-fire ceramic (LTCC) material.

7. The IMD of claim 6, wherein the LTCC material has a melting point between about 850 C.° and 1150 C°.

8. The IMD of claim 1, wherein at least one of the dielectric layers comprises a high temperature co-fire ceramic (HTCC) material.

9. The IMD of claim 8, wherein the HTCC material has a melting point between about 1100 C.° and 1700 C°.

10. The IMD of claim 1, wherein the at least one conductive via includes an impedance that is selected to achieve a desired impedance for the 3D antenna.

11. The IMD of claim 1, wherein a via of the at least one conductive via is represented by a plurality of separate sub-vias having respective cross-sectional areas, wherein the via includes a cross-sectional area represented by the collection of respective cross-sectional areas of the separate sub-vias.

12. The IMD of claim 1, further comprising a cavity formed in the monolithic structure derived from a plurality of discrete dielectric layers with respect to the 3D antenna to enable radio frequency (RF) impedance matching.

13. The IMD of claim 1, wherein the first and second portions of the 3D antenna pattern and the at least one conductive via are formed from a biocompatible conductive material.

14. The IMD of claim 1, further comprising a header block, wherein the monolithic antenna structure is positioned within the header block.

15. The IMD of claim 1, wherein the monolithic structure is attached to a housing for the IMD using at least one of a brazing, glassing, diffusion bonding or other bonding technique that provides a hermetic seal between the structure and the housing.

16. The device of claim 1, wherein the housing is an RF ground plane.

17. The device of claim 1, wherein the RF module is electrically connected to the monolithic antenna structure by a feedthrough bridging the housing and the monolithic structure.

18. An implantable medical device ("IMD") comprising:
  a housing defining an interior cavity;
  a monolithic antenna structure derived from a plurality of discrete dielectric layers having an antenna, interconnects and impedance matching elements embedded within the monolithic antenna structure, wherein the antenna includes an antenna pattern, a first portion of the antenna pattern positioned under a selected one of the plurality of dielectric layers, a second portion of the antenna pattern positioned over the selected one of the plurality of dielectric layers, and at least one conductive via extending through the selected one of the plurality of dielectric layers that connects the first portion of the antenna pattern to the second portion of the antenna pattern; and
  a radio frequency (RF) module disposed within the interior cavity of the housing and electrically connected to the antenna, wherein the antenna is configured to convert electromagnetic power of a downlink telemetry transmission of an external telemetry antenna into a signal that the RF module can process and to convert uplink telemetry signals generated by the RF module into electromagnetic power of an uplink telemetry transmission.

19. The IMD of claim 18, wherein the at least one conductive via serves as the impedance matching elements embedded within the monolithic antenna structure.

20. The IMD of claim 18, further comprising at least one cavity formed in the monolithic antenna structure to provide embedded radio frequency (RF) impedance matching functionality for the antenna.

21. The IMD of claim 18, wherein at least one of the dielectric layers comprises a ceramic material, further wherein the dielectric layers, the antenna and the impedance matching elements are co-fired together into the monolithic antenna structure.

22. The IMD of claim 18, further comprising surface mounted impedance matching elements mounted on a surface of the monolithic antenna structure for providing additional impedance matching functionality.

* * * * *